US00PP28831P3

(12) United States Plant Patent
Brand et al.

(10) Patent No.: US PP28,831 P3
(45) Date of Patent: Jan. 2, 2018

(54) ***ARONIA* PLANT NAMED 'UCONNAM166'**

(50) Latin Name: ***Aronia melanocarpa*×*A. mitschurinii***
Varietal Denomination: UCONNAM166

(71) Applicant: University of Connecticut, Farmington, CT (US)

(72) Inventors: Mark Henry Brand, Willington, CT (US); Bryan Allan Connolly, Mansfield Center, CT (US)

(73) Assignee: University of Connecticut Technology Commercialization Services

( * ) Notice: Subject to any disclaimer, the term of this patent is extended or adjusted under 35 U.S.C. 154(b) by 31 days.

(21) Appl. No.: 14/998,768

(22) Filed: Feb. 10, 2016

(65) Prior Publication Data

US 2017/0231133 P1 Aug. 10, 2017

(51) Int. Cl.
*A01H 5/00* (2006.01)

(52) U.S. Cl.
USPC ..... Plt./156

(58) Field of Classification Search
USPC ..... Plt./226, 156
CPC ..... A01H 5/00; A01H 5/02; A01H 5/0216
See application file for complete search history.

(56) References Cited

PUBLICATIONS

Missouri Botanical Garden *Aronia melanocarpa* 'Morton', retrieved on May 2, 2017, retrieved from the Internet at <http://www.missouribotanicalgarden.org/PlantFinder/PlantFinderDetails.aspx?kempercode=c622> 2 pp.*

Proven Winners Low Scape Hedger *Aronia melanocarpa* 2017, retrieved on May 2, 2017, retrieved from the Internet at <https://www.provenwinners.com/plants/aronia/low-scape-hedger-aronia-melanocarpa> 3 pp.*

Spring Meadow Nursery, Inc. Flowering Shrubs Starter Plants Catalog and Shrub Reference 2015-2016, retrieved on May 2, 2017, retrieved from Internet at <http://springmeadownursery.com/content-media/catalog_2015.pdf> pp. 1-6, 12, 33 and 100.*

* cited by examiner

*Primary Examiner* — June Hwu
(74) *Attorney, Agent, or Firm* — Cassandra Bright

(57) ABSTRACT

A new and distinct *Aronia* cultivar named 'UCONNAM166' is disclosed, characterized by a distinctly upright plant form, reaching a mature height between 4 to 5 feet. Vigorous but controlled plant growth. Multicolored Fall foliage. Plants are adaptable to a variety of landscape uses, including hedging or mass planting. Triploid plants produce very few, or no fruits. The new variety is a *Aronia*, normally produced as an outdoor landscape plant.

2 Drawing Sheets

Figure 1:
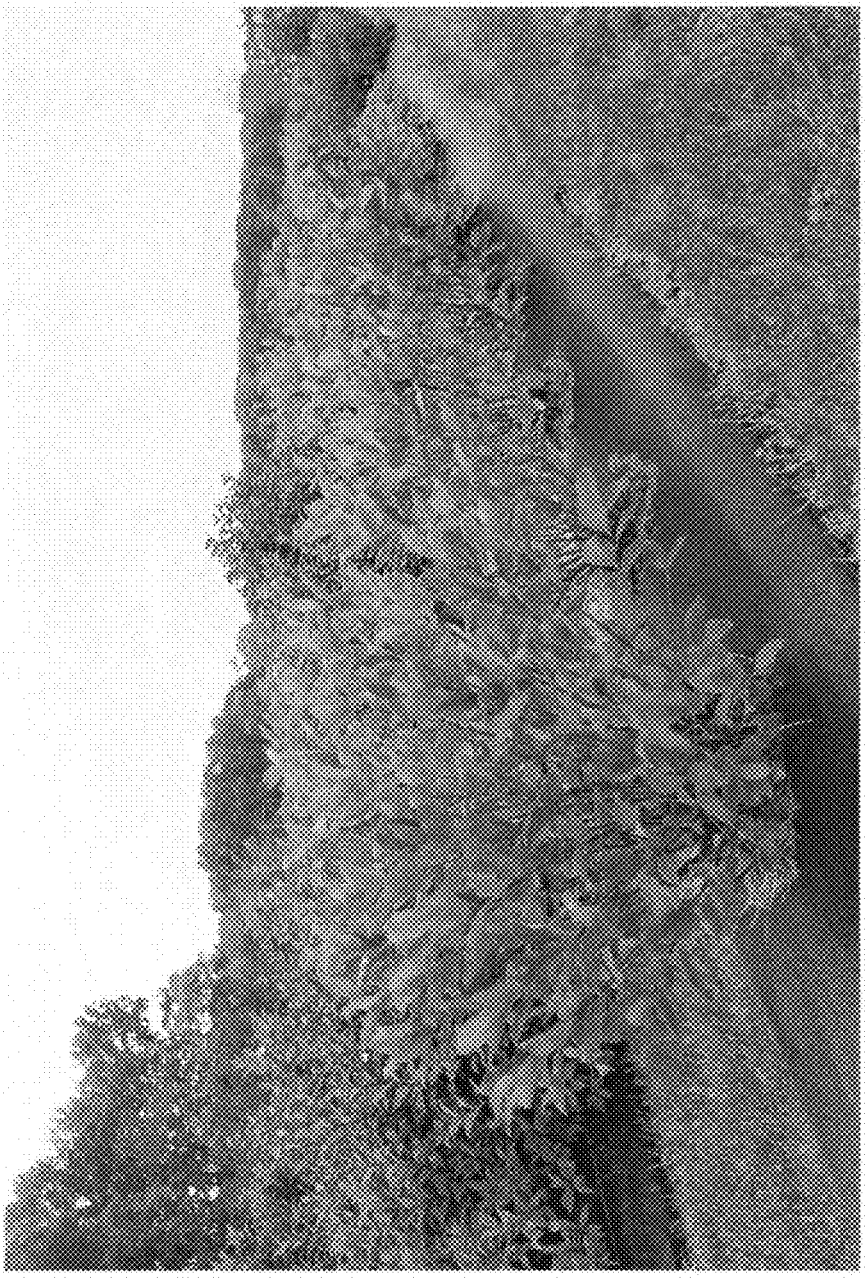

This invention was made with government support under grant number 58-1230-7-439 awarded by the United States Department of Agriculture. The government has certain rights in the invention.

Latin name of the genus and species: *Aronia melanocarpa*×*A. mitschurinii.*

Variety denomination: 'UCONNAM166'.

BACKGROUND OF THE INVENTION

The new *Aronia* cultivar is a product of a planned breeding program conducted by the inventors, Mark Henry Brand and Bryan Allan Connolly in Storrs, Conn. The objective of the breeding program was to produce new *Aronia* varieties like 'Viking' but with narrower and shorter form. The cross resulting in this new variety was made during May of 2010.

The seed parent is the, unpatented variety referred to as *Aronia melanocarpa* 'UC012'. The pollen parent is the unpatented variety *Aronia mitschurinii* 'Viking'. The new variety was discovered in June of 2011 by the inventors in a group of seedlings resulting from the 2010 crossing, in a greenhouse in Storrs, Conn.

Asexual reproduction of the new cultivar 'UCONNAM166' by nodal initiation tissue culture was first performed during the June of 2011, at a laboratory in Storrs, Conn. Subsequent propagation by softwood cuttings has shown that the unique features of this cultivar are stable and reproduced true to type in 3 successive generations.

SUMMARY OF THE INVENTION

The cultivar 'UCONNAM166' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'UCONNAM166' These characteristics in combination distinguish 'UCONNAM166' as a new and distinct *Aronia* cultivar:

1. Distinctly upright form, 4-5' tall by 3' wide. Shoots are vertical.
2. Leaves are larger than typical for *Aronia melanocarpa*. Leaves are slightly smaller than leaves of *Aronia mitschurinii* 'Viking', but have a similar appearance to 'Viking'.
3. Vigorous growth, but not as vigorous as *Aronia mitschurinii* 'Viking'.
4. Fall foliage color is multi-colored, orange, red, and yellow.
5. Adaptable, easy to grow, full sun to partial shade.

6. Good for hedge applications or mass planting in challenging landscape situations.
7. White flowers in clusters in early may (Connecticut).
8. Triploid plants with little or no fruit production.

PARENT COMPARISON

Plants of the new cultivar 'UCONNAM166' are similar to plants of the seed parent, *Aronia melanocarpa* 'UC012' in most horticultural characteristics, however, plants of the new cultivar 'UCONNAM166' differ in the following;

1. 4-5' tall by 3' wide, while the seed parent is 1-2' tall and 3-4' wide.
2. Upright, vertical habit, no rhizomes, while the seed parent is prostrate, with a highly rhizomatous growth habit.
3. Light to moderate flowering, while the seed parent is moderate to heavy flowering.
4. Leaves are large sized, while the seed parent has small to medium sized leaves.
5. Minimal or no berries, while the seed parent has black berries.

Plants of the new cultivar 'UCONNAM166' are similar to plants of the pollen parent, *Aronia melanocarpa* 'Viking' in most horticultural characteristics, however, plants of the new cultivar 'UCONNAM166' differ in the following;

1. 4-5' tall by 3' wide, while the pollen parent is 6-8' tall and 6-8' wide.
2. Upright, vertical habit, while the pollen parent is of somewhat loose, open spreading form.
3. Short internodes, while the pollen parent has long internodes.
4. Leaves are large sized, while the pollen parent has very large leaves.
5. Minimal or no berries, while the pollen parent has black berries.

COMMERCIAL COMPARISON

Plants of the new cultivar 'UCONNAM166' can be compared to the unpatented commercial variety *Aronia* 'Morton' (Iroquois Beauty). These varieties are similar in most horticultural characteristics; however, 'UCONNAM166' differs in the following:

1. 4-5' tall by 3' wide, while the comparator is 2-3' tall and 5-7' wide.
2. Upright, vertical habit, no rhizomes, while the comparator is upright spreading habit with rhizomes.
3. Leaves are large sized, while the comparator has medium sized leaves.
4. Minimal or no berries, while the comparator has black berries.

Plants of the new cultivar 'UCONNAM166' can also be compared to the unpatented commercial variety *Aronia* 'Autumn Magic'. These varieties are similar in most horticultural characteristics; however, 'UCONNAM166' differs in the following:

1. 4-5' tall by 3' wide, while the comparator is 5-6' tall and 5-7' wide.
2. Upright, vertical habit, no rhizomes, while the comparator is upright spreading habit with rhizomes.
3. Leaves are large sized, while the comparator has medium sized leaves.
4. Minimal or no berries, while the comparator has black berries.

BRIEF DESCRIPTION OF THE PHOTOGRAPHS

The accompanying photograph in FIG. 1 illustrates in full color typical plants of 'UCONNAM166' grown outdoors, in Mansfield, Conn.

Figure 2:
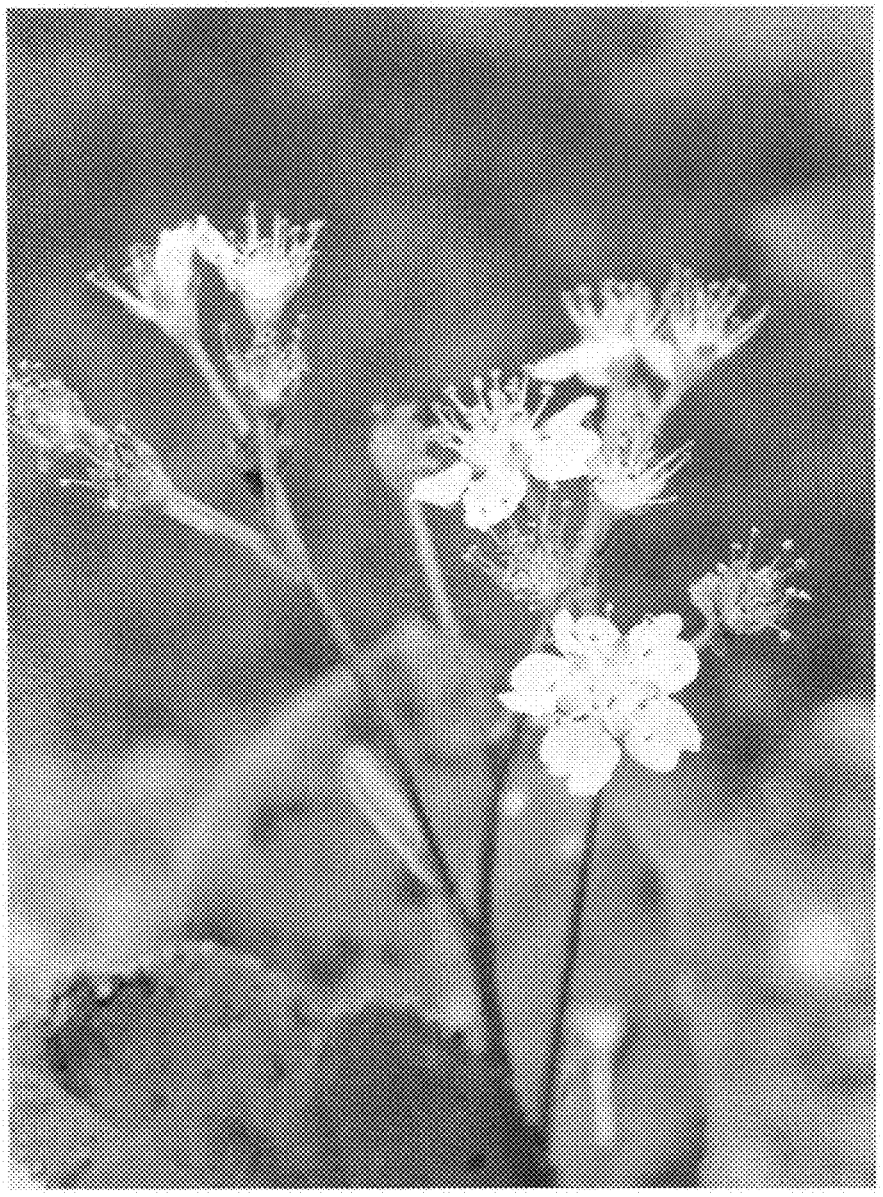

FIG. 2 illustrates in full color a typical inflorescence of 'UCONNAM166'. Age of the plant photographed is approximately 3 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'UCONNAM166' plants grown in poly house in Grand Haven, Mich., under natural lighting. Measurements were taken during April of 2015. The plants were 2-3 years old in 3 gallon containers. The growing temperature ranged from 5° C. to 27° C. Measurements and numerical values represent averages of typical plant types.

Botanical classification: *Aronia melanocarpa*×*A. mitschurinii* 'UCONNAM166'.

PROPAGATION

Time to initiate roots: About 3 weeks at approximately 24° C.

Time to produce a rooted young plant: About 8 weeks at 24° C.

Roots: Moderate density moderate branching. Medium thickness, fibrous and white in color, not accurately measured with The R.H.S. Chart.

PLANT

Plant type: Perennial shrub.
Age of plant described: Approximately 2-3 years old.
Growth habit: Upright and compact.
Pot size of plant described: 3 gallon pot.
Appropriate containers sizes: 1, 2, and 3 gallon pots.
Overall plant shape: Upright.
Height: 92 cm.
Plant spread: 92 cm.
Growth rate: Moderate.
Plant vigor: Good.
Branching characteristics: Upright occurring branches, with basal branching.
Length of primary lateral branches: 90 cm.
Diameter of lateral branches: 5 mm.
Quantity of lateral branches: 20-30.
Internode length: 4.5 cm.
Stem:
- *Stem appearance*.—Round.
- *Stem strength*.—Moderate.
- *Stem color*.—New growth: Near RHS Greyed-Orange 166B. 1-year-old growth: Near RHS Greyed-Orange 177B. Old Growth: Near RHS Yellow-Green 152A.
- *Pubescence*.—Yes.
- *Aspect*.—80-90° very upright Other plant characteristics: Lenticels: 1-2 mm Near RHS Greyed-Orange 164B.

FOLIAGE

Leaf:
*Arrangement*.—Alternate, single.
*Leaf shape*.—Elliptic.
*Average length*.—9-10 cm.
*Average width*.—5-6 cm.
*Apex*.—Acute to cuspidate.
*Base*.—Between cuneate and obtuse.
*Margin*.—Crenate.
*Texture of top surface*.—Smooth.
*Texture of bottom surface*.—Slightly rough/waxy.
*Leaf side with pubescence*.—Under side.
*Color*.—Young foliage upper side: Near RHS Yellow-Green 144A. Young foliage under side: Near RHS Yellow-Green 146D. Mature foliage upper side: Near RHS Green 137A. Mature foliage under side: Near RHS Yellow-Green 146C.
*Fall foliage*.—Upper side: Near RHS Red 43B. Flushed and blotched Yellow 13B. Under side: Near RHS Red 43D flushed Orange 25C. Blotched Yellow 13B.
*Venation*.—Pattern: Pinnate. Color upper side: Midrib: Near RHS Yellow-Green 146D. Veins: Near RHS Green 137A. Color under side: Midrib: Near RHS Yellow-Green 146D. Veins: Near RHS Yellow-Green 146C.
*Petiole*.—Average Length: About 1 cm. Diameter: 1-3 mm. Petiole color upper side: Near RHS Yellow-green 146D. Petiole color lower side: Near RHS Yellow-green 146D. Petiole Texture upper side: Canaliculate/smooth. Petiole Texture lower side: Canaliculate/smooth.

FLOWER

Natural flowering season: Spring.
Inflorescence type and habit: Upright compound corymb.
Inflorescence height: 2-3 cm.
Inflorescence width: 2-3 cm.
Quantity of flowers per inflorescence: 5-10.
Quantity of flowers per lateral stem: 30-40.
Quantity of flowers per plant: 80-300.
Flower longevity on plant: 1-2 weeks.
Individual flowers:
*Flower form*.—Rotate.
*Flower shape*.—Radial.
*Flower aspect*.—Upright.
*Flowering habit*.—Upright and outwardly facing.
*Size*.—Diameter: 12 mm. Length: 12 mm. Depth: 6 mm.
Flower other characteristics:
*Persistence*.—Self cleaning.
*Fragrance*.—Slight.
Petal:
*Petal arrangement*.—Whorled.
*Petal appearance*.—Spade-like.
*Number of petals per flower*.—5.
*Petal fused*.—No.
*Petal shape*.—Circular.
*Petal base*.—Attenuate.
*Margin*.—Entire.
*Tip shape*.—Rounded.
*Length*.—5 mm.
*Width*.—4 mm.
*Texture*.—Upper: Glabrous. Lower: Glabrous.
Petal color:
*When opening*.—Upper surface: Near RHS White 155B. Lower surface: Near RHS White 155B with some Red-Purple 62C.
*Fully opened*.—Upper surface: Near RHS White 155B. Lower surface: Near RHS White 155B.
Bud:
*Shape*.—Spherical.
*Length*.—5 mm.
*Diameter*.—4 mm.
*Color*.—Near RHS White 155B and Greyed-Purple 186B.
Sepals:
*Arrangement*.—Radial.
*Number*.—5.
*Shape*.—Deltate.
*Base*.—Truncate.
*Margin*.—Entire.
*Tip shape*.—Acute.
*Length*.—1 mm.
*Width*.—1 mm.
*Color upper*.—Near RHS Green 139D.
*Color lower*.—Near RHS Green 139C.
*Texture*.—Upper: Pubescent. Lower: Glabrous.
Calyx:
*Shape*.—Radial.
*Length*.—3 mm.
*Diameter*.—5.5 mm.
Peduncle:
*Length*.—7 mm.
*Diameter*.—1 mm.
*Color*.—Near RHS Yellow-Green 146D.
*Strength*.—Good.
*Texture*.—Glabrous.

REPRODUCTIVE ORGANS

Stamens:
*Number*.—18.
*Filament length*.—4 mm.
*Filament color*.—Near RHS White 155B.
Anthers:
*Shape*.—Dorsifixed.
*Length*.—1 mm.
*Color*.—Near RHS Red-Purple 59B.
*Pollen color*.—Brown.
*Pollen amount*.—Little-moderate.
Pistil:
*Number*.—4.
*Length*.—3 mm.
*Style*.—Length: 1 mm. Color: Near RHS Yellow-Green 146D.
*Stigma*.—Shape: Syncarpous fused stigma with 3-5 lobes. Color: Near RHS Yellow-Green 146D. Ovary Color: Near RHS Yellow-Green 146D.

OTHER CHARACTERISTICS

Fruit: Not observed. The new variety is a triploid and assumed sterile.
Disease/pest resistance: Typical of the species.
Temperature tolerance: The new variety tested to temperatures between −25° C. to 40° C.

What is claimed is:

1. A new and distinct cultivar of *Aronia* plant named 'UCONNAM166' as herein illustrated and described.

* * * * *